United States Patent
Oxenkrug et al.

(10) Patent No.: US 6,353,015 B1
(45) Date of Patent: Mar. 5, 2002

(54) METHOD OF TREATING NEURODEGENERATIVE DISORDERS

(75) Inventors: Gregory F. Oxenkrug, Newton, MA (US); Sergei O. Bachurin; Andrey Zakharovic Afanasiev, both of Chernogolovka (RU); Pura J. Requintina, West Kinsington, RI (US)

(73) Assignee: St. Elizabeth's Medical Center, Boston, MA (US)

( * ) Notice: Subject to any disclaimer, the term of this patent is extended or adjusted under 35 U.S.C. 154(b) by 0 days.

(21) Appl. No.: 09/673,451

(22) PCT Filed: Aug. 25, 1999

(86) PCT No.: PCT/US99/19584

§ 371 Date: Mar. 23, 2001

§ 102(e) Date: Mar. 23, 2001

(87) PCT Pub. No.: WO00/12045

PCT Pub. Date: Mar. 9, 2000

Related U.S. Application Data

(60) Provisional application No. 60/097,967, filed on Aug. 26, 1998.

(51) Int. Cl.[7] ............................................. A61K 31/405
(52) U.S. Cl. ...................................................... 514/415
(58) Field of Search ......................................... 514/415

(56) References Cited

U.S. PATENT DOCUMENTS

| | | | |
|---|---|---|---|
| 3,642,994 A | * | 2/1972 | Anton-Tay |
| 5,284,862 A | | 2/1994 | Bigge et al. |
| 5,491,153 A | | 2/1996 | Salituro et al. |
| 5,700,828 A | * | 12/1997 | Federowicz et al. |
| 6,011,054 A | | 1/2000 | Oxenkrug et al. |
| 6,063,805 A | | 5/2000 | Oxenkrug et al. |
| 6,239,162 B1 | | 5/2001 | Oxenkrug |

OTHER PUBLICATIONS

Iacovitti et al, Chemical Abstracts on STN, abstract No. 127:257849, 1997.*

* cited by examiner

*Primary Examiner*—William R. A. Jarvis
(74) *Attorney, Agent, or Firm*—Nixon Peabody LLP

(57) ABSTRACT

This invention relates to the use of N-acetyl-serotonin (NAS) derivatives for the treatment and prophylaxis of neurological injury and neurodegenerative disorders in a mammal.

33 Claims, 8 Drawing Sheets

METHOD OF TREATING NEURODEGENERATIVE DISORDERS

This application is a 371 of PCT/US99/19584, filed Aug. 25, 1999, which claims priority to provisional application 60/097,967, filed Aug. 26, 1998.

BACKGROUND OF THE INVENTION

1. Field of the Invention

The present invention relates to a method of treatment or prophylaxis of neurological injury and neurodegenerative disorders in a mammal, particularly a human being. This method comprises the administration of a therapeutically effective amount of an N-acetylserotonin (NAS) derivative to the mammal.

2. Background

Nerve cell death (degeneration) can cause potentially devastating and irreversible effects for an individual and may occur e.g. as a result of stroke, heart attack or other brain or spinal chord ischemia or trauma. Additionally, neurodegenerative disorders-involve nerve cell death (degeneration) such as Alzheimer's disease, Parkinson's disease, Huntington's disease, Amyotrophic Lateral Sclerosis, Down's Syndrome and Korsakoff's disease.

Therapies have been investigated to treat nerve cell degeneration and related disorders, e.g., by limiting the extent of nerve cell death that may otherwise occur to an individual. See, e.g., N. L. Reddy et al., *J. Med. Chem.*, 37:260–267 (1994); and WO 95/20950.

The compound MK-801 has exhibited good results in a variety of in vivo models of stroke. See B. Meldrum, *Cerebrovascular Brain Metab. Rev.*, 2:27–57 (1990); D. Choi, *Cerebrovascular Brain Metab. Rev.*, 2:105–147 (1990). See also Merck Index, monograph 3392, 11th ed., 1989. For example, MK-801 exhibits good activity in mouse audiogenic tests, a recognized model for evaluation of neuroprotective drugs. See, e.g., M. Tricklebank et al., *European Journal of Pharmacology*, 167:127–135 (1989); T. Seyfried, *Federation Proceedings*, 38(10):2399–2404 (1979).

However, MK-801 also has shown toxicity and further clinical development of the compound is currently uncertain. See J. W. Olney et al., *Science*, 244:1360–1362 (1989); W. Koek et al., *J. Pharmacol. Exp. Ther.*, 252:349–357 (1990); F. R. Sharp et al., *Society for Neuroscience Abstr.*, abstr. no. 482.3 (1992).

It thus would be highly desirable to have new neuroprotective agents, particularly agents to limit the extent or otherwise treat nerve cell death (degeneration) such as may occur with stroke, heart attack or brain or spinal cord trauma, or to treat neurodegenerative disorders such as Alzheimer's disease, Parkinson's disease, Huntington's disease, Amyotrophic Lateral Sclerosis, Down's Syndrome and Korsakoff's disease.

Shuttle-box avoidance performance of vehicle-treated rats (n=11), AF64A-treated rats and AF64A-treated rats receiving Melatonin or CA-15 (3 mg/kg, once daily, 12–14 days, orally; n–10), where n is the number of rats in each group.

A. Learning test. Following 20 acquisition trials, rats were given 3 blocks of 5 trials.

B. Retention test. Two blocks of 5 trials were given 24 h after learning trial.

Data are presented as mean±SEM percentage of correct responses summarized over each block; –$p<0.05$, *–$p<0.001$, vs. AF64A-treated group, where p is the significance level, * p—not significant (post hoc ANOVA).

Figure 5B:
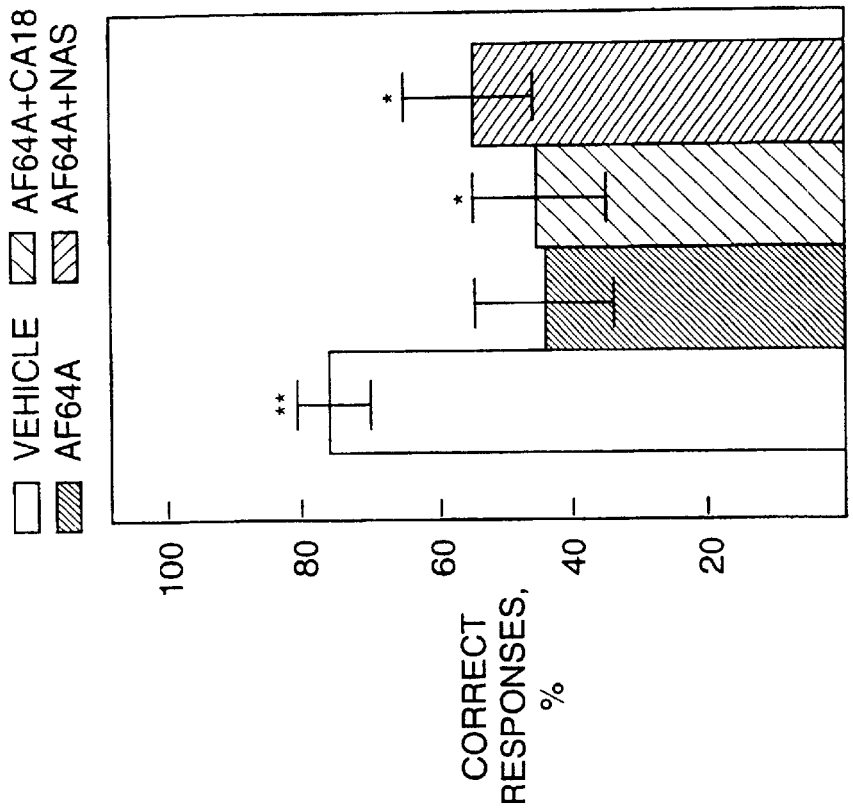
Figure 5A:
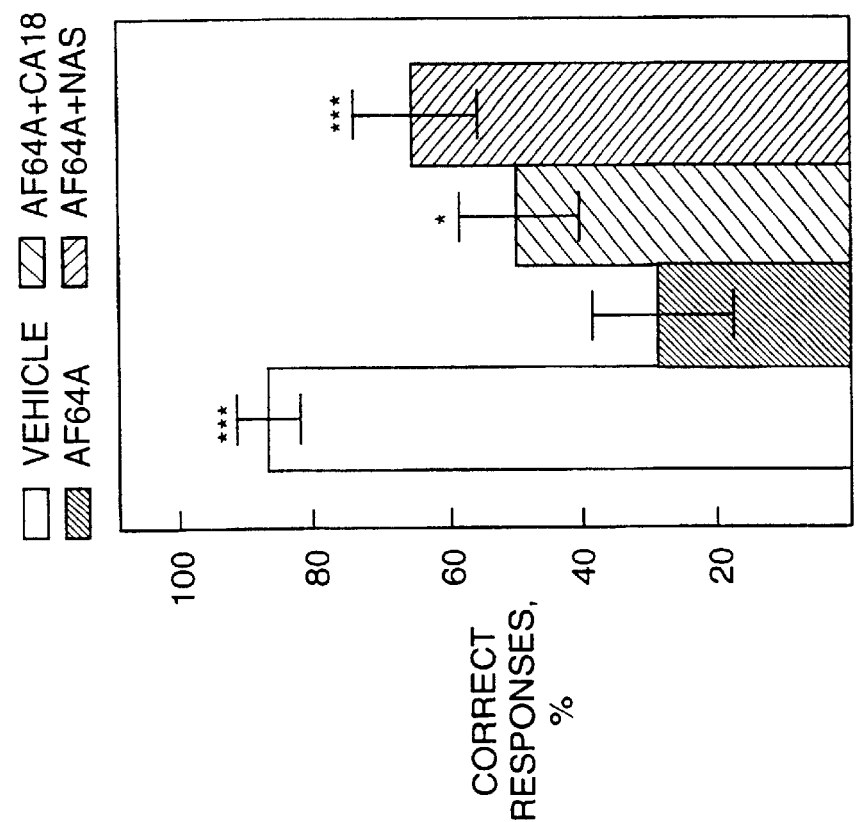

FIGS. 5A and 5B Illustrate the cognition enhancing effect of CA18 and NAS.

Shuttle-box avoidance performance of vehicle-treated rats (n=11), AF64A-treated rats and AF64A-treated rats receiving NAS or CA-18 (1 mg/kg, once daily, 12–14 days, orally; n=10), where n is the number of rats in each group.

A. Learning test. Following 20 acquisition trials, rats were given 3 blocks of 5 trials.

B. Retention test. Two blocks of 5 trials were given 24 h after learning trial. Data are presented as mean±SEM percentage of correct responses summarized over each block; –$p<0.05$, *–$p<0.001$ vs. AF64A-treated group, where p is the significance level, *—not significant (post hoc ANOVA).

Figure 6B:
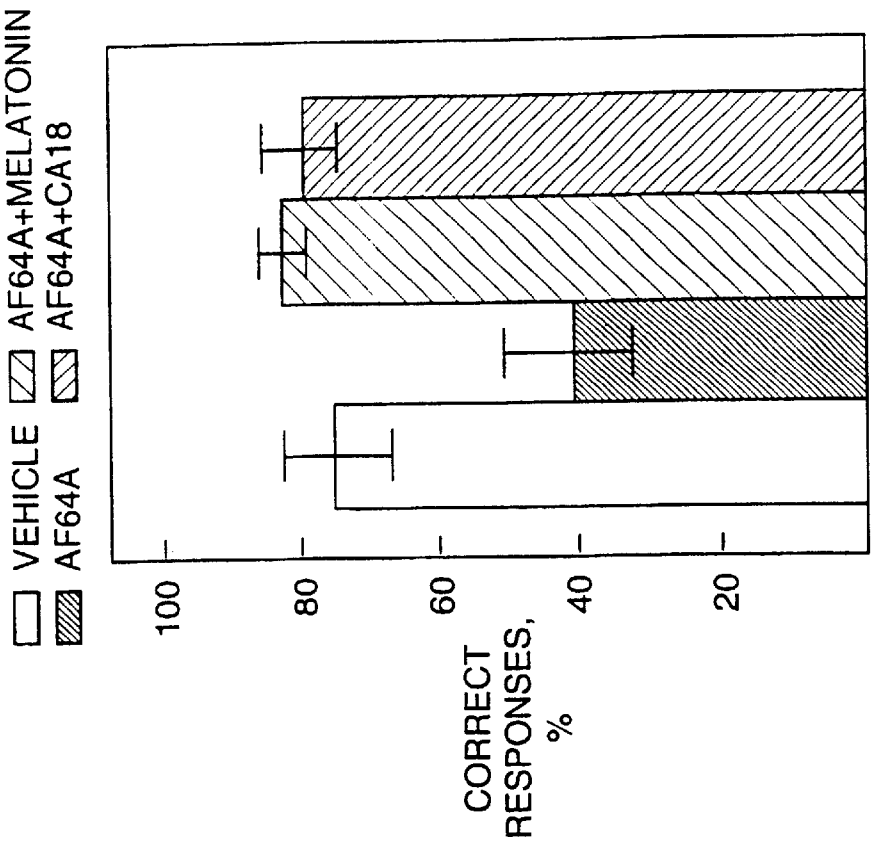
Figure 6A:
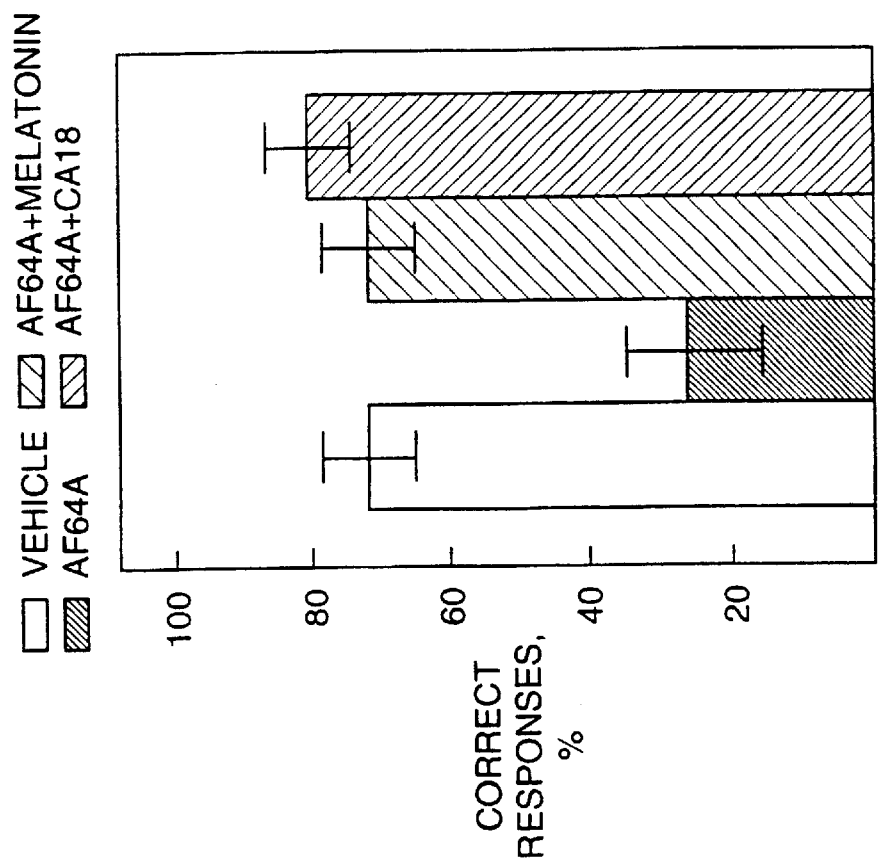

FIGS. 6A and 6B Illustrate the cognition enhancing effect of melatonin and CA18.

Shuttle-box avoidance performance of vehicle-treated rats (n=11), AF64A-treated rats (n=10) and AF64A-treated rats receiving Melatonin or CA-18 (0,3 mg/kg, once daily, 12–14 days, orally,; n=11), where n is the number of rats in each group.

A. Learning test. Following 20 acquisition trials, rats were given 3 blocks of 5 trials.

B. Retention test. Two blocks of 5 trials were given 24 h after learning trial.

Data are presented as the mean±SEM percentage of correct responses summarized over each block; $p<0.001$, where p is the significance level. The values of p illustrate that there was a significant difference in avoidance performance vs. AF64A-treated group (post hoc ANOVA).

Figures 7A, 7B:
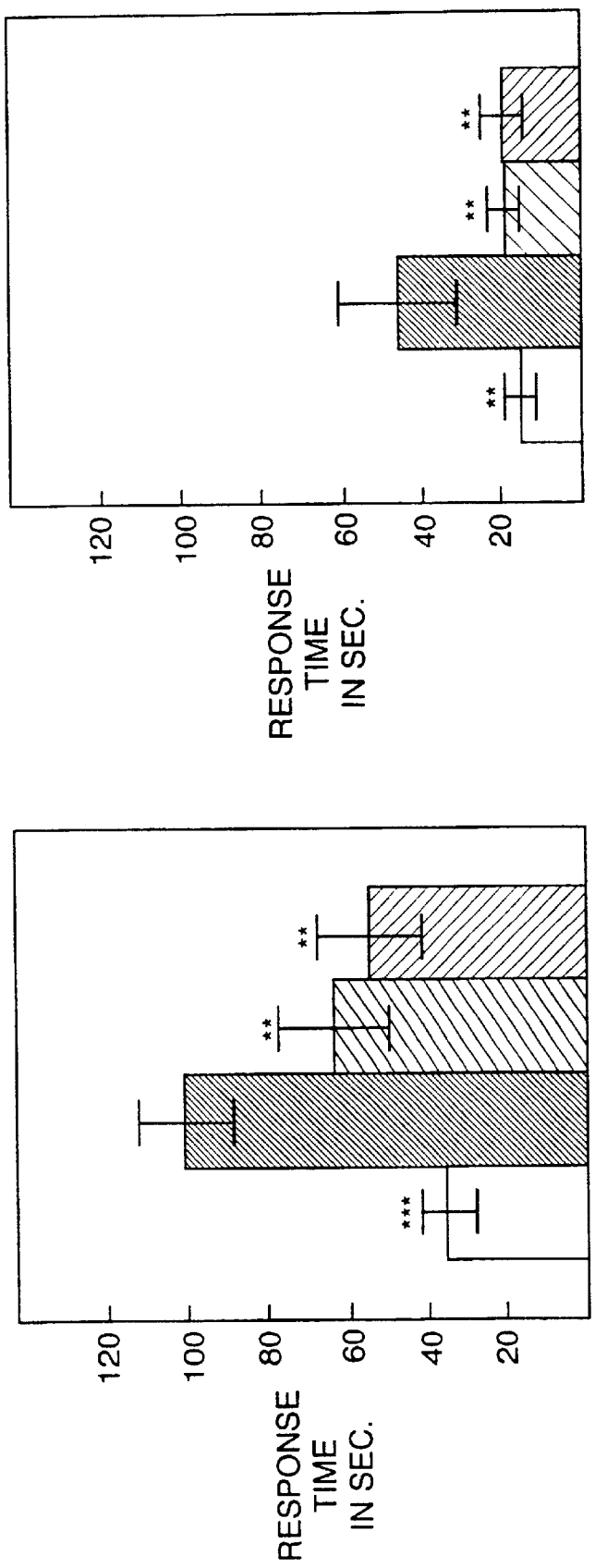

FIGS. 7A and 7B Average swim latency made by rats, when trained 1 (A) and 30 (B) 5 days to find a platform in Morris water maze test. Performance of vehicle-treated rats (n=11), AF64A-treated rats (n=10) and AF64A-treated rats receiving melatonin or CA-18 (0,3 mg/kg, once daily, 12–14 days, orally; n=11) was started 3 days after the last injection of compound and was performed daily during the period from 3rd up to 7th day (n is the number of rats in each group). Results were estimated as time required for rat felt into a water pool to reach a platform;–p<5 0.05, *–$p<0.001$ vs. AF64A-treated group, where p is the significance level (post hoc ANOVA).

Figure 8:
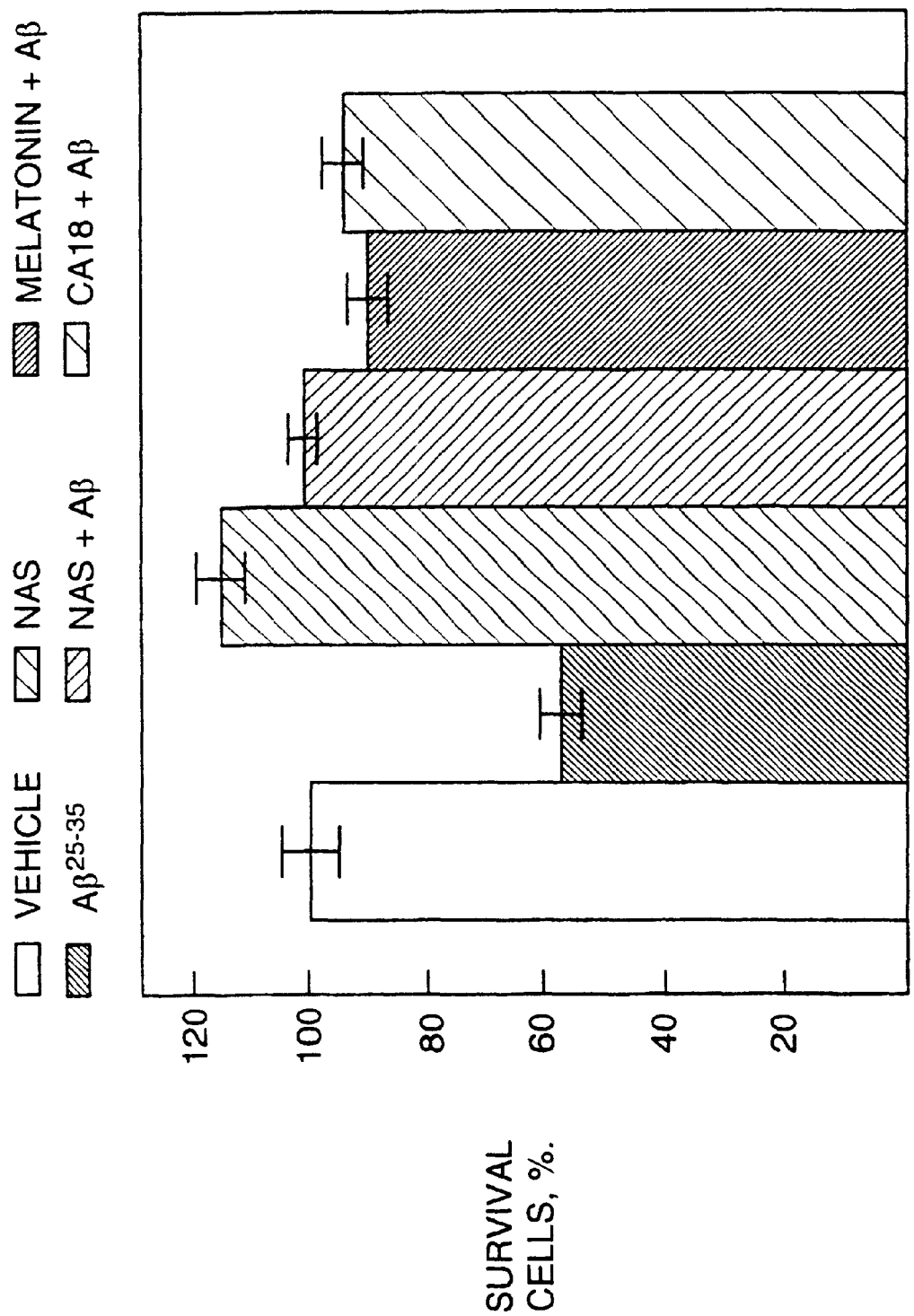

FIG. 8. Protective effect of N-Acetyl-Serotonin (NAS), Melatonin and CA-15 against the toxicity of βAP 25–35 in mature cultures of cerebellar granule cells. Cultures, 8 days in vitro (DIV) were treated with vehicle, 25 mM βAP, 25 mM βAP and 25 mM NAS, or 25 mM melatonin, or 25 mM CA-15 for 4 days. The difference in numbers of living neurons before and after 4 days of treatment were determined. The amount of viable neurons is expressed as mean (%) above viable in preliminary photography of the same place. Experiments were repeated 2–3 times (n=12–18). For graphical presentation, average data from representative experiments were converted to percentages of control groups viability. Results were expressed as a percentage of survival cells to compare with control ±SEM and were analyzed by a statistical test (ANOVA).

SUMMARY OF THE INVENTION

The present invention relates to a method of treatment or prophylaxis of neurological injury and neurodegenerative disorders in a mammal, preferably a human being. This method comprises the administration of a therapeutically effective amount of N-acetyl-serotonin (NAS) or an NAS derivative or a pharmaceutically acceptable salt thereof, to the mammal. The NAS derivative may be administered alone or in combination with other agents.

N-acetyl-serotonin (NAS) derivatives useful in the methods of the present invention include a compound of the following Formula I:

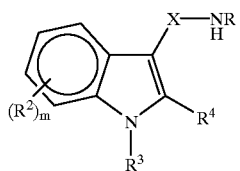

I wherein R is —C(=O)R$^1$, —S(O)$_2$R$^1$ or S(O)R$^1$;

R$^1$ is optionally substituted allyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroaynylene; each R$^2$ is independently optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

R$^3$ and R$^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

Additionally, NAS derivatives useful in practicing the present invention include a compound of the following Formula II:

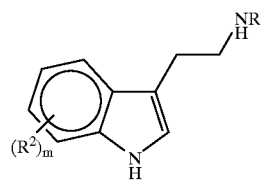

wherein R is —C(=O)R$^1$ or —S(O)$_2$R$^1$;

is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each R$^2$ is independently hydrogen, optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable salts thereof.

NAS derivatives useful in practicing the present invention further include a compound of the following Formula III:

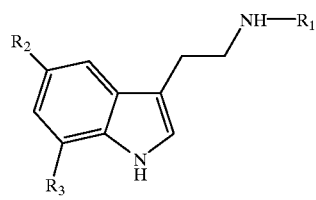

I wherein R$^1$ is low Alk—SO$_2$—or; R$^4$—CO—(wherein R$^4$ is low Alk—, low AlkO—, low Alk—NH);

R2 is H, Alk, halogen, R$^5$)— (where R$^5$=H, low Alk, PhCH$_2$—); and

R3 is H or Me.

The present invention includes methods for treatment and/or prophylaxis of neurological conditions/injuries such as epilepsy, neurodegenerative conditions and/or nerve cell death (degeneration) resulting from e.g. hypoxia, hypoglycemia, brain or spinal chord ischemia, retinal ischemia, brain or spinal chord trauma or post-surgical neurological deficits and the like. The present invention also includes treatment of a person susceptible or suffering from stroke or heart attack or neurological deficits relating to cardiac arrest, a person suffering or susceptible to brain or spinal cord injury, or a person suffering from the effects of retinal ischemia or degeneration. The methods of the present invention are useful to treat and/or prevent various neurodegenerative diseases such as Parkinson's disease, Huntington's disease, Amyotrophic Lateral Sclerosis, Alzheimer's disease, Down's Syndrome, Korsakoff's disease, cerebral palsy and/or age-dependent dementia. The methods of the present invention are also useful in the prevention of age-associated cognitive decline.

DETAILED DESCRIPTION OF THE INVENTION

The present invention relates to a method of treatment or prophylaxis of neurological injury and neurodegenerative disorder in a mammal, preferably a human being. The method comprising administering a therapeutically effective amount of the above-defined Formulae I, II and III or a pharmaceutically acceptable salt thereof, to a mammal in reed thereof or a member of a population susceptible thereto.

Suitable halogen substituent groups of compounds of Formulae I, II and III as defined above (i.e. compounds of the invention) include F, Cl, Br and I. Alkyl groups of compounds of the invention typically have from 1 to about 12 carbon atoms, more preferably 1 to about 8 carbon atoms, still more preferably 1 to about6 carbon atoms, even more preferably 1, 2, 3 or 4 carbon atoms, or still more preferably 1, 2 or 3 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkylthio groups of compounds of the invention include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazol. Suitable hetefoalicyclic groups of compounds of the invention contain one or more N, O or S atoms and include, e.g., tetrahydrofuranyl, thienyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,5-substituted phenyl, 2,3,5-substituted and 2,4,5-substituted phenyl; and substituted naphthyl, including naphthyl substituted at the 5, 6 and/or 7 positions. Preferred substituents of such substituted carbocyclic groups are identified below.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl).

As discussed above, X groups of Formula I suitably are alkylene or heteroalkylene linkages, or may contain one or more carbon-carbon double or triple bonds, i.e. alkenylene, alkynylene, heteroalkenylene or heteroalkynylene linkage. Such unsaturated X group typically contain 1, 2, 3 or 4 carbon-carbon multiple bonds, more typically 1 or 2 carbon-carbon multiple bonds. An X group that is heteroalkylene, heteroalkenylene or heteroalkynylene contains one or more N, O or S atoms in the chain between amino group and R3 group of Formula I, with other atoms in the chain suitably being carbons. Typically a heteroalkylene, heteroalkenylene or heteroalkynylene X group contain 1–3 N, 0 or atoms in the chain, more typically 1 or 2 N, O or S atoms. Typically an X group contains from about 1 to 6 carbon atoms.

Suitable cyclic alkyl groups include groups having five or six or more ring carbon atoms, particularly optionally substituted adamanyl, isobornyl, norbornyl, cyclohexyl, cyclopentyl and the like. Generally preferred cyclic alkyl groups have from 5 to about 10 ring members. Cyclic alkyl groups having bridged structures, such as adamantyl, are particularly preferred.

As discussed above, $R^1$, X, $R^2$, $R^3$ and $R^4$ groups of compound of the invention are optionally substituted. A "substituted" $R^1$, X, $R^2$, $R^3$ and $R^4$ group or other substituent may be substituted at one or more available positions, typically 1 to 3 or 4 positions, by one or more suitable groups such as those disclosed herein. Suitable groups that may be present on a "substituted" $R^1$, X, $R^2$, $R^3$ and $R^4$ or other substituent include e.g. halogen such as fluoro,chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e.g. an R group being a substituted or unsubstituted biphenyl moiety); and aralkyl such as benzyl.

Preferred carbocyclic ring substituents of compounds of the invention include halogen (F, Cl, Br and I); hydroxyl; azido; optionally substituted alkyl having 1 to about 6 carbons such as methyl, ethyl, propyl and butyl and branched groups such as isopropyl, sec-butyl and tert-butyl, and including halogenated alkyl, particularly fluoro-alkyl having 1 to about 6 carbon atoms; optionally substituted alkoxy having 1 including halogenated alkoxy, particularly fluoro-alkoxy having 1 to about 6 carbon atoms; optionally substituted alkylthio having 1 to about 6 carbons such as methylthio and ethylthio; optionally substituted alkylsulfinyl having 1 to about 6 carbons such as methylsulfinyl (—S(O)CH$^3$) and ethylsulfinyl (—S(O)CH$^2$CH$^3$); optionally substituted alkylsulfonyl having 1 to about 6 carbons such as methylsulfonyl (—S(O)$_2$CH$_3$) and ethylsulfonyl (—S(O)$_2$CH$_2$CH$_3$); and optionally substituted arylalkoxy such as benzyloxy (C$_6$H$_5$CH$_2$O—).

It should be understood that alkoxy, alkylthio, alkylsulfinyl, alkylsulfonyl and aminoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Without wishing to be bound by theory, compounds of the invention that contain an alkylsulfinyl and/or alkylsulfonyl group, may be, in effect, "pro-drugs" wherein after administration of the compound to a subject the sulfinyl or sulfonyl group(s) are metabolized (reduced) in vivo to the corresponding sulfide moiety.

Specifically preferred compounds of the invention include the following:

N-[2-(5-Benzyloxyindol-3-yl)ethyl]propanamide

N-[2-(5-Benzyloxyindol-3-yl)ethyl] butanamide

As discussed above, the present invention includes methods for treating or preventing certain neurological disorders, including the consequences of stroke, heart attack and traumatic head or brain injury, epilepsy or neurodegenerative diseases comprising the administration of an effective amount of one or more compounds of the invention to a subject including a mammal, particularly a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extra-corporal circulation such as e.g. a bypass procedure.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurysm or hemorrhage. Thus, an effective amount of one or more compounds of the present invention could be administered pre-operatively or peri-operatively to reduce such risks associated with carotid endarterectomy, or other post-surgical neurological deficits.

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of one or more compounds of the invention, typically either pre-operatively or peri-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of one or more compounds of the invention, typically either pre-operatively or peri-operatively.

The invention further provides a method of treating Korsakoff's disease, a chronic alcoholism-induced condition, comprising administering to a subject including a mammal, particularly a human, one or more compounds of the invention in an amount effective to treat the disease. Compounds of the invention are anticipated to have utility for the attenuation of cell loss associated with Korsakoff's disease.

The invention also includes methods for treating a person suffering from or susceptible to cerebral palsy, emesis, narcotic withdrawal symptoms and age-dependent dementia, comprising administering to a subject including a mammal, particularly a human, one or more compounds of the invention in an amount effective to treat the condition.

Compounds of the invention may be used in therapy in conjunction with other medicaments. For example, for treatment of a stroke victim or a person susceptible to stroke, one or more compounds of the invention may be suitably administered together with a pharmaceutical targeted for interaction in the blood clotting mechanism such as streptokinase, tPA, urokinase and other agents that lyse clots. Also, one or more compounds of the invention may be administered together with agents such as heparin and related heparin-based compounds, acenocoumarol or other known anticoagulants.

Compounds of the invention also may function as pro-drugs and may be metabolized in vivo to forms of enhanced activity.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Compounds of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampoules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma., As discussed above, typical candidates for treatment include heart attack, stroke, brain or spinal cord injury patients, patients undergoing major surgery where brain or spinal cord ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of the invention particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day.

The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage, preferably from 0.2 to 2 milligrams per unit dosage.

When used in medicine, the salts of the NAS derivatives should be pharmaceutically acceptable acid addition salts, but pharmaceutically unacceptable salts may conveniently be used to prepare the base or pharmaceutically acceptable salts of the base, and are not excluded from the scope of this invention. Suitable pharmaceutically acceptable salts include, but are not limited to, those prepared from the following acids: hydrochloric, hydrobromic, hydroiodic, sulfuric, nitric, phosphoric, maleic, salicylic, p-toluenesulfonic, tartaric, citric, acetic, methanesulfonic, formic, succinic, naphthalene-2-sulfonic, isethionic, lactobionic and benzenesulfonic.

The NAS derivatives may be prepared by those methods known in the art. NAS may be purchased commercially from, for example, Sigma Chemical Company.

The entire text of all documents cited herein are incorporated by reference herein. The following non-limiting examples are illustrative of the invention.

This invention has been described in detail with reference to preferred embodiments thereof. However, it will be appreciated that those skilled in the art, upon consideration of this disclosure, may make modifications and improvements within the spirit and scope of the invention.

EXAMPLES

Synthesis

Example 1

N-[2-(5-Benzyloxyindol-3-yl)ethyl]propanamide (DNAS-15 or CA-15)

Propionic anhydride (0.3 ml, 2.3 mmol) was added dropwise at room temperature to a well-stirred mixture of 5-benzyloxytryptamine hydrochloride (0.605 g, 2 mmol), $Et_3N$ (0.65 ml, 4.6 mmol) and $CH_2Cl_2$ (5 ml). After stirring for 24 h, the reaction mixture was washed with water (2.5 ml), 5% solution of $NaHCO_3$ (10 ml), 1% solution of HCl (5 ml) and then saturated solution of NaCl (10 ml). After drying over $Na_2SO_4$, the solvent was evaporated. Recrystallization of residue from benzene-heptane gave a yield of 0.515 g (80%) of N-[2-(5-benzyloxyindol-3-yl)ethyl] propanamide: mp 110–112° C. $^1H$ NMR($CDCl_3$, ppm, δ): 1.11(3H, t, $CH_2CH_3$, J=8 Hz), 2.13(2H, q, $CH_2CH_3$), 2.90 (2H, t, β-$CH_2$, J=6.7 Hz), 3.58 (2H, q, α-$CH_2$, J=6.2 Hz), 5.10(2H, s, $CH_2$—O), 5.59(1H, bs, NH), 6.86–7.04(2H, m, 2- and 6-H), 7.13(1H, d, 4-H, $J_{4-6}$=2Hz), 7.25–7.68(6H, m 7-H and Ph), 8.15(1H, bs, 1-H). Found, %: C 74.23; H 6.75; N 8.77. $C_{20}H_{22}N_2O_2$. Calc., %: C 74.53; H 6.83; N 8.70%.

Example 2

N-[2-(5-Benzyloxyindol-3-yl)ethyl] butanamide (DNAS-18 or CA-18)

Butyric anhydride (0.2 ml, 1.2 mmol) was added dropwise at room temperature to a well-stirred mixture of 5-benzyloxytryptamine hydrochloride (0.3 g, 1 mmol), $Et_3N$ (0.35 ml, 2.5 mmol) and $CH_2Cl_2$ (3 ml). After stirring for 40 h at 30–35° C. the reaction mixture was washed with water (2×5 ml), 5% solution of $NaHCO_3$ (2×10 ml), 1% solution of HCl (5 ml) and then saturated solution of NaCl (10 ml). After drying over $Na_2SO_4$, the solvent was evaporated. Recrystallization of residue from benzene-heptane gave a yield of 0.25 g (74%) of N-[2-(5-benzyloxyindol-3-yl)ethyl] butanamide: mp 112–114° C. $^1H$ NMR($CDCl_3$, ppm, δ): 0.90(3H, t, $CH_2C\underline{H}_3$, J=8 Hz), 1.39(2H, m $CH_2C\underline{H}_2$ $CH_3$), 2.07(2H, t, $C\underline{H}_2CH_2$ $CH_3$, J=8 Hz), 2.92(2H, t, β-$CH_2$, J=7 Hz), 3.56 (2H, q, α-$CH_2$, J=6.5 Hz), 5.05(2H, s, $CH_2$-O); 5.63(1H, bs, NH), 6.90–7.00(2H, m, 2- and 6-H), 7.10(1H, d, 4-H, $J_{4-6}$=2 Hz), 7.20–7.48(6H, m, 7-H and Ph), 8.24(1H, bs, 1-H). Found, %: C 75.23; H 6.95; N 8.37. $C_{21}H_{24}N_2O_2$. Calc., %: C 75.0; H 7.14; N 8.33%.

Example 3

Methods

Rats were trained to avoid electrofootshock applied 20 seconds after turning lights on in one of the two chambers of the two-way shuttle box (Lermontova, et al., 1998). Memory function was evaluated in a "learning" test conducted on the same day as the training experiment, while "retention" abilities were evaluated in the test conducted the day after the training experiments. Cholinergic neurotoxin, AF64A, was injected intracerebraventriculary (i.c.v.) (3 nmol/ventricle). DNAS-15 (3 mg/kg p.o.) was administered for 12 days after AF64A injections. Control animals received injections of artificial cerebrospinal fluid (i.c.v.) or vehicle (p.o.). Each group consists of 7 animals. Results were expressed as mean±s.d. The difference between the groups were analyzed by one-way ANOVA and Student t-test.

Results

Figure 1:
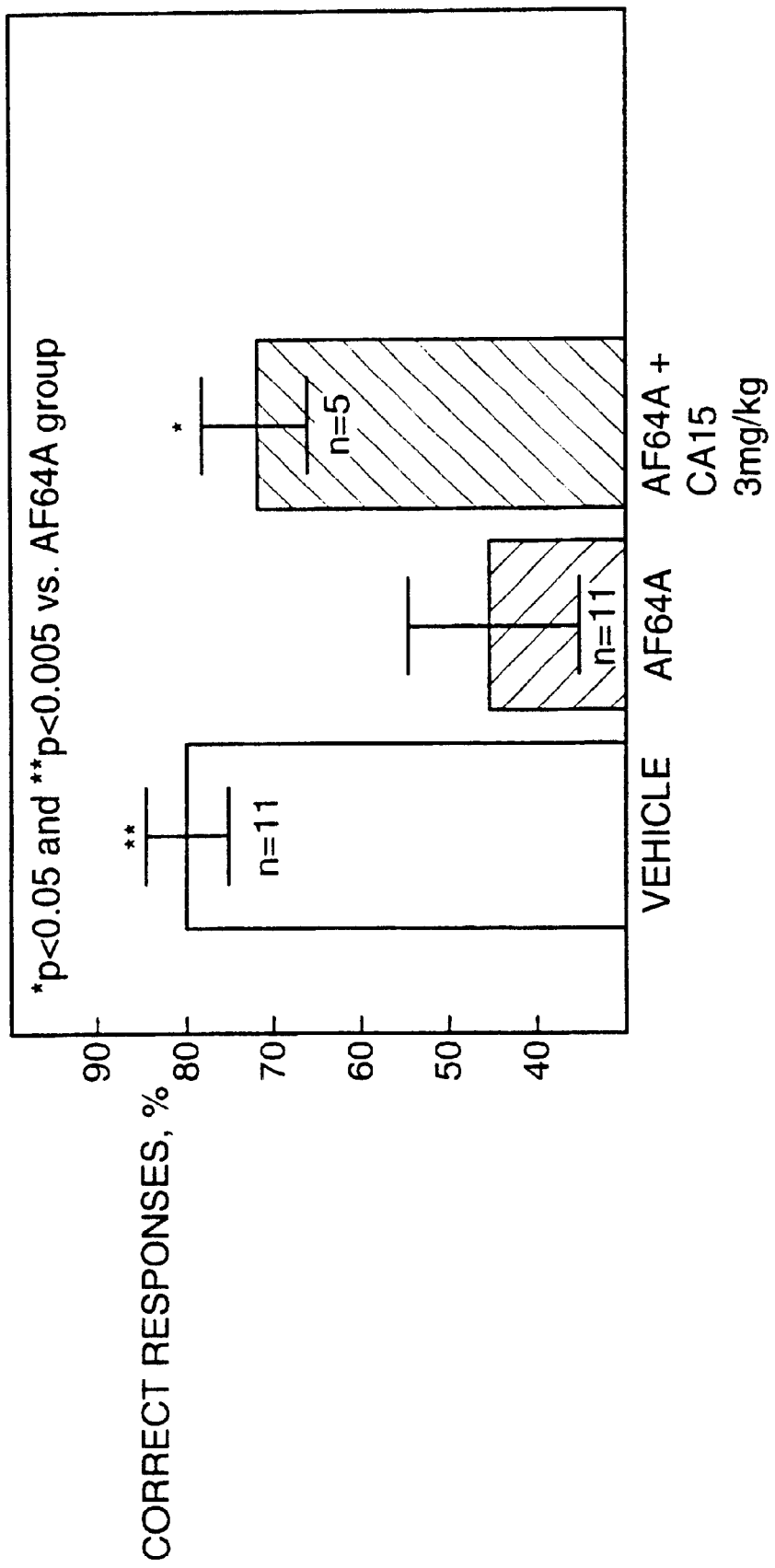
FIG. 1. Illustrates the cognition enhancing effect of CA-15 as measured by the learning test.
Figure 2:
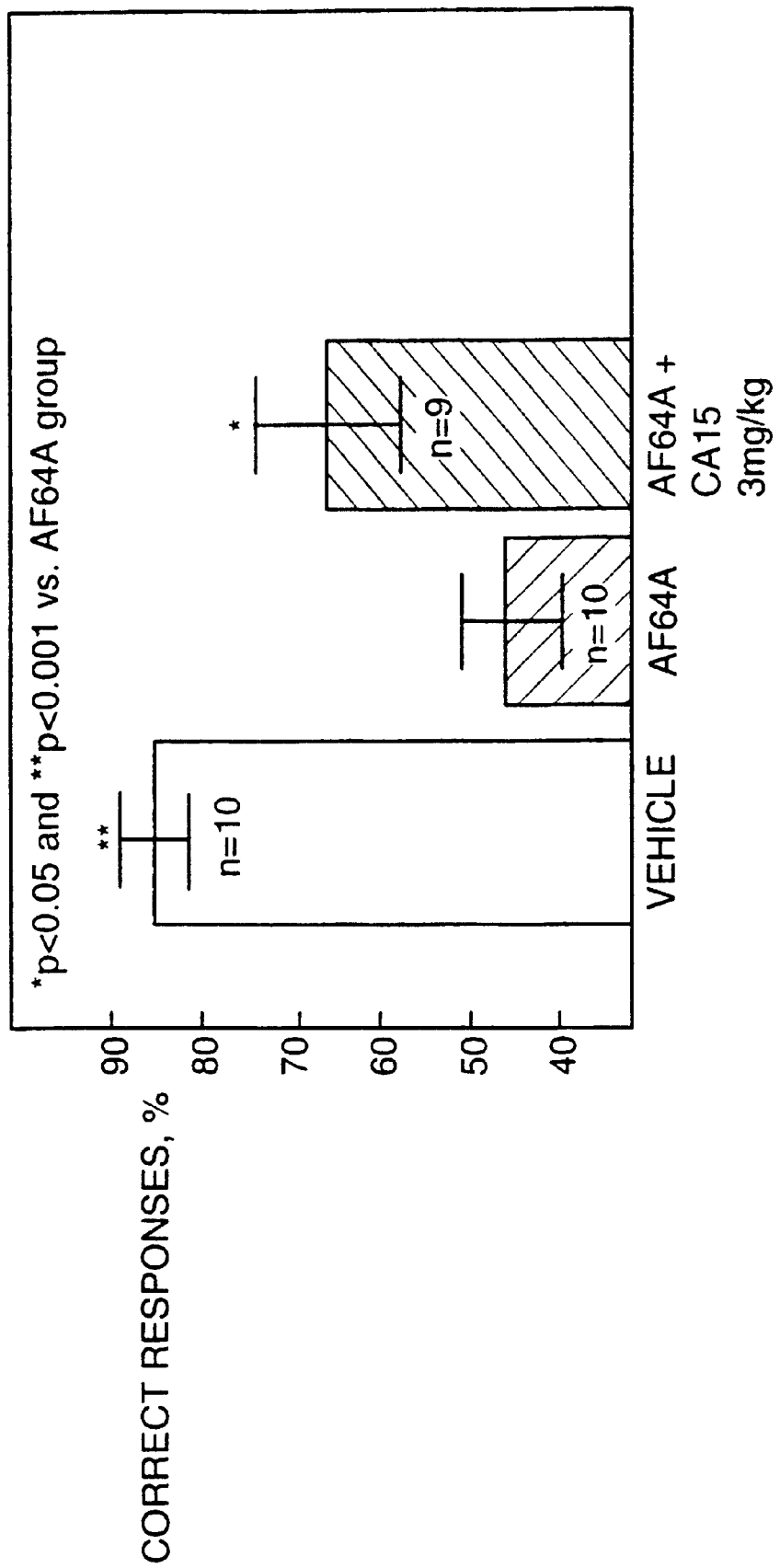
FIG. 2. Illustrates the cognition enhancing effect of CA-15 as measured by the retention test.
Figure 3:
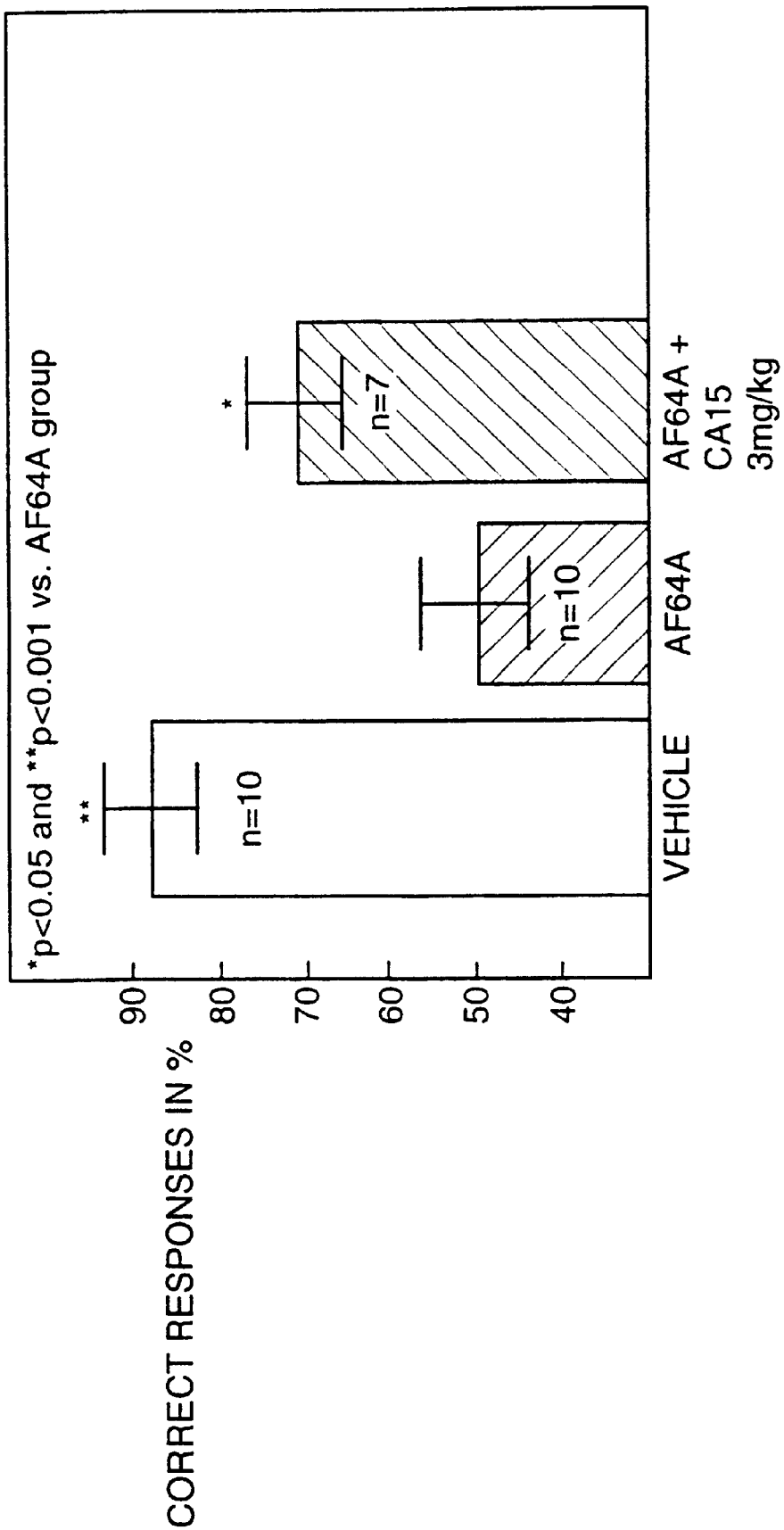
FIG. 3. Illustrates the cognition enhancing effect of CA-15 as measured by the retention test, ten days after the learning trials.

Administration of AF64A dramatically decreased the number of correct responses in learning and retention tests (FIGS. 1–3).

DNAS-15 almost completely restored the number of correct responses in these tests (FIGS. 1 and 2). The cognition-enhancing effect of DNAS-15 in retention test lasted, at least, for 10 days after the learning trials (FIG. 3).

Discussion

The present results are the first demonstration of the positive effects of NAS derivatives on cognitive function in rats. The ability of DNAS-15 to counteract the impairing effect of cholinergic toxin, AF64A, on the learning and retention functions suggests the neuroprotective properties of DNAS-15 (and other related NAS derivatives). Such properties might suggest the possibility of clinical use of NAS derivatives for prevention and treatment of age-associated cognitive decline, Alzheimer's and other types of dementia, Parkinson's disease and other degenerative disease effecting brain tissues, the other possible use might be the treatment of stroke and brain injury victims.

Example 4

Methods

Cerebellar granule cells (CGC) obtained from brains of 8-day rat pups were maintained in culture. The amyloid beta-protein (βAP) and/or NAS derivative (DNAS-18) were added to CGC for a period of 72 hr. Vehicle solution was added to CGC in the control experiments. Survival of CGS was assessed by lactate dehydrogenase method and by visual counting of living neurons.

Results

Incubation with DNAS-18 (25 mM) increased the viability of CGC neurons by 18±3% of control (mean±S.E.).The viability of CGC neurons with βAP (25 mM) was 56±8% of control (mean±S.E.).

Addition of DNAS-18 (25 mM) to neurons incubated with βAP (25 mM) increased the viability of neurons to 98±4% of control (p<0.00 1).

Discussion

The neuronal death induced by βAP is currently considered as one of the main causative mechanisms of the development of Alzheimer's dementia, and possibly, age-associated cognitive decline. The results set forth above are the first demonstration of the ability of NAS derivatives to counteract the neuronal death, induced by the βAP. Thus, NAS derivative(s) are useful in prevention of age-associated cognitive decline and for the treatment of Alzheimer's dementia.

Example 5

N-Acetyl-serotonin, melatonin and their derivatives improve cognition and protect against β-amyloid-induced neurotoxicity.

It is known that dysfunction of circadian rhythms in Alzheimer's Disease (AD) can be compensated by exogenous melatonin (W. Witting et al., Biol. Psych 27:563–572, 1990). It was also suggested that positive effect of chronic prophylactic administration of melatonin as gerontoprotector is based on its antioxidative properties (R. J. Reiter et al., Annals New York Acad. Sci. 362–378, 1996). Numerous studies indicate that melatonin as a free radical scavenger displays pronounced neuroprotective effects against neurotoxic action of the excitatory amino acids (excitotoxicity) and toxic effect of beta-amyloid peptide (βAP)—one of the specific hallmarks of AD (M. A. Papolla et al., J. Neurosci. 17:1683–1690, 1997). Recently neuroprotective activity was revealed for the melatonin precursor N-acetylserotonin (NAS) (B. Longoni et al., Biochem. Biophys. Res. Comm., 233:778–780, 1997). Since neurodegenerative processes in AD are associated with the decreased cognitive functions, it was reasonable to study the effect of melatonin, NAS and their newly synthesized derivatives on cognitive functions in animal models of AD-type neurodegeneration.

In the present study both in vivo and in vitro models were used. The in vivo study involved the neurotoxin-induced animal model of AD, based on observation that intracerebroventricular (i.c.v.) administration of ethylcholine aziridinium ion (AF64A) produced chronic cholinergic hypofunction and learning and memory impairment in rat analogous to that observed in AD (A. Fisher et al., Ann. Rev. Pharmacol. Toxicol., 26:161–181, 1986). Currently this model is used also for screening of the compounds for their potential cognition-enhancing properties (T. Walsh et al., In Toxin-Induced Models of Neurological Disorders. M. I. Woodruff, A. J. Nonneman (eds) Plenum Press, New York, London. pp 259–279, 1994; N. N. Lermontova et al., Molec. Chem. Neuropathol. 33:51–51, 1998). At the cellular level (in vitro) the adequate model of AD-type degeneration is believed to be the neuronal cell culture degeneration induced by βAP-fragment 25–35 (I. Gozes et al., Proc. Natl. Acad. Sci. USA 93:427–453, 1996). In the present study we examined cognition-enhancing and neuroprotective properties of melatonin, NAS and their newly synthesized derivatives CA-15 and CA-18 in the above mentioned animal and cell models of AD-type neurodegeneration.

Methods

Chemicals

β-Amyloid peptide—fragment 25–35 of βAP. Melatonin, NAS and CA-15 and CA-18 were preliminary dissolved in DMSO and diluted by water each day prior to use.

Animals

Male Wistar rats (12–16 weeks old, 280–450 g) were used in behavioral experiments. Rats were kept at 12 hrs light :12 hrs dark schedule (lights on/off at 4:00/16:00 h) with the free access to water and food.

Rats were anaesthetized with ether and placed into a stereotaxic frame before the surgery. Freshly prepared from AF64 solutions of AF64A (3 nmol/3 μl) or vehicle (cerebrospinal fluid, CSF) were injected into each of lateral cerebral ventricles. After surgery, rats were given a recovery period (12 days) before being tested in behavioral experiment. Melatonin;

NAS and their derivatives were administrated orally (in starch solutions) once a day around the time of circadian light-off during all the recovery period.

Behavioral Studies.

1a. Active Avoidance Test.

Training was conducted in a two-chamber shuttle box according to the procedure described earlier (N.N. Lermontova et al., *Molec. Chem. Neuropathol.* 33:51–51, 1998). The conditioned stimulus was a 5 sec light followed by the unconditioned stimulus, a 1 mA shock which was delivered to the grid in the lit chamber. The rat avoided the shock by crossing through to the other (dark) chamber. The avoidance during the conditioned stimulus was considered as a correct response. Training procedure consisted of 35 trials (learning test). Fifteen further trials were given 24 h later (retention test).

1b. Statistical Treatment.

Each experimental group, i.e., control, AF64A-treated groups and groups for each concentration of the tested compounds, contained 9–11 rats. Data of the number of correct responses from the last 15 trials of the first 35 trials (learning test) or first 15 trials of the retention test were collected for each rat. The mean ±SEM of correct responses was calculated for total number of rats in groups. Data was analyzed as the mean ±SEM in percentage of maximum possible number of correct responses (=100%) by ANOVA followed by post hoc comparisons.

2a. Morris Water Maze Test.

The test was started 2 days after the last injection of tested compounds and was performed daily for the period from 3 to 9 day. Round swimming pool (1,8 m diameter and 0,45 m high) with 22° C. water was placed in the center of the room. The platform was located 1 cm below the surface of the water. Starting points for the swims were at the cardinal compass points (N, S, E, W), which were selected in a semi-random fashion for each rat on each trial.

2b. Statistical Treatment.

Each experimental group, i.e., control, AF64A-treated groups and groups for each concentration of the tested compounds, contained 9–11 rats. Results were estimated as time required for rat felt into a water pool to reach a platform (a sum of two trials from different position every day). Data were analyzed as the mean±SEM. (ANOVA followed by post hoc comparisons).

3. Neuronal Cell Culture.

Cerebellar granule cells (CGC) were prepared from the postnatal rats (7–8 days old) by the following procedure based on the generally accepted methods (V. Gallo et al., *J. Neurosci.* 7:2203–2213, 1987). The pieces of cerebellum were digested with 0,25 mg/ml trypsin for 25 min. at 37° C. and incubated for 5 min. in 0.1% soybean trypsin inhibitor. After washing, cells were dissociated by triturating. Following two centrifugation-resuspension steps, the cells were plated at a density of 2.5–5×10 cells per ml on polylysine-coated 24-well plates (Corning) and maintained at 37° C. in a humidified incubator with 5% $CO_2$/95% room air. The medium was composed of Eagle's minimal essential medium and fetal calf serum (10%) supplemented with 20 mM potassium chloride, 10 mM glucose, 2 mM glutainine, 50 μg/ml gentamycin sulfate. Cytosine arabinoside (10 μM) was added 24–48 h later to prevent the replication of non-neuronal cells.

4a. Toxicity Assays.

The neurotoxic and neuroprotective effects of NAS, melatonin and their derivatives were tested in mature cultures at 7–8 days in vitro (7–8 DIV) after changing of medium to a fresh medium without serum with Supplement N1 (Sigma). The βAP 25–35 (Bachem) was dissolved by sonication in sterilized distilled water at a concentration of 1 mM. Solutions of all reagents were added to the wells with cultures at 25 μM and the effect was observed during the next days by microscopy.

4b. Quantitative Assessment.

Neuronal viability was evaluated by morphometric cell counting using the presence of neurites and smooth, round cell bodies as criteria of survival. The cells were examined under the phase-contrast microscope Axiovert 25C with videocamera and Software miroMedia PCTV VideoCap program for image scanning and photography. Cell survival was quantified by counting the number of viable neurons in premarked microscope fields prior to, and 4 days after the exposure. The difference in numbers of living neurons before and after 4 days of treatment was determined.

4c. Statistical Analysis.

For each experiment, we used 4–6 separate wells of a 24-well multiwell plate for control (with 0.05% DMSO)and for each concentration of compound or composition of compound with βAP. Each well equals one observation, (average of 25 cells per microscope field). Experiments are repeated 2–3 times (n=12–18). For graphical presentation, average data from representative experiments were expressed as a percentage of survival cells in comparison with control ±SEM and analyzed by ANOVA and Student t-test.

RESULTS

Active Avoidance Test.

AF64A (3 nmol/3 microl, i.c.v.) dramatically decreased rats performance in learning and retention paradigms of the active avoidance test (FIGS. 4–6) and Table 1. Table 1. demonstrates the influence of melatonin, NAS, and its O-benzyl hormologues on active avoidance performance by the AF64A-treated rats. In this instance, rats were treated intracerebroventricularly (i.c.v.) AF64A (3 nmol/3 μl) or CSF (control groups) and were given a recovery period (12–14 days) before being tested in behavioral experiments. The experimental rats were given the studied compounds orally during the recovery period. Shuttle-box avoidance performance: Learning test—following 20 acquisition trials, rats were given three blocks of five trials. Retention test— two blocks of five trials were given 24 h after the learning trial. Data are presented as the mean ±SEM percentage of correct responses summarized over each block and were analyzed by statistical tests (ANOVA). *–$p<0.001$, **–$p<0.05$ vs. AF64A-treated group.

Furthermore, NAS (1 mg/kg, p.o., daily) improved the performance of AF64A-treated rats in learning (FIG. 5A) but not in retention (FIG. 5B) paradigms of the active avoidance test. Melatonin effect was studied in two doses: 0.3 mg/kg and 3 mg/kg (p.o., daily). The lower dose of melatonin (0.3 mg/kg,) completely restored rats performance in the learning (FIG. 6A) and retention (FIG. 6B) paradigms of the active avoidance test. The cognitive-enhancing effect of a higher dose of melatonin (3 mg/kg) was significant but somewhat less pronounced than the effect of the lower dose (0.3 mg/kg) (FIGS. 4A and 4B).

Figure 4B:
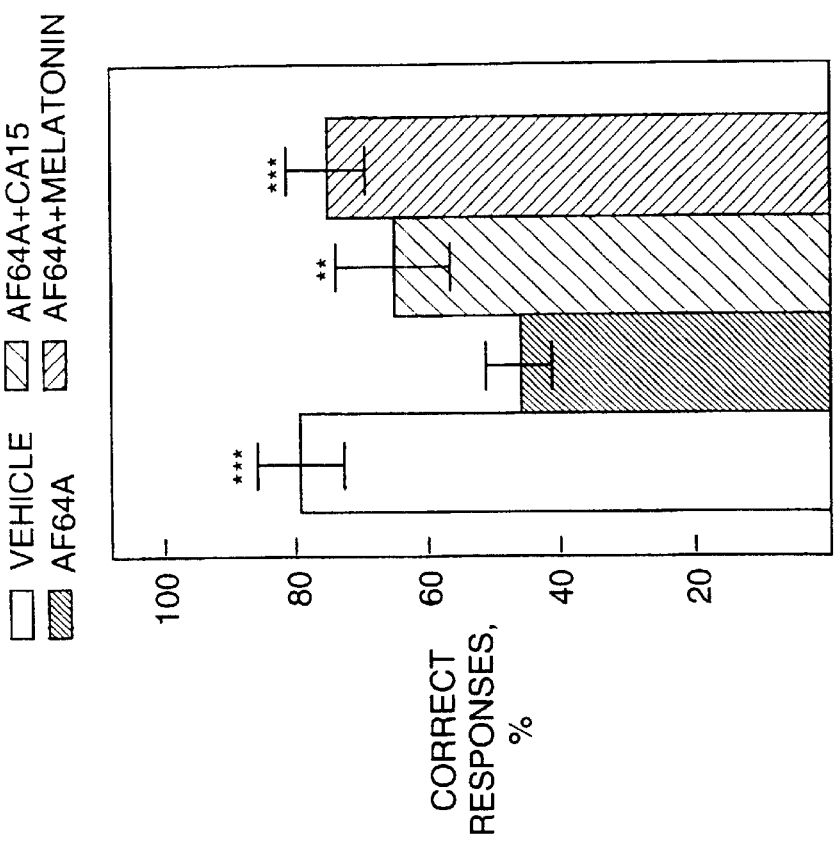
FIGS. 4A and 4B Illustrate the cognition enhancing effect of melatonin and CA15.
Figure 4A:
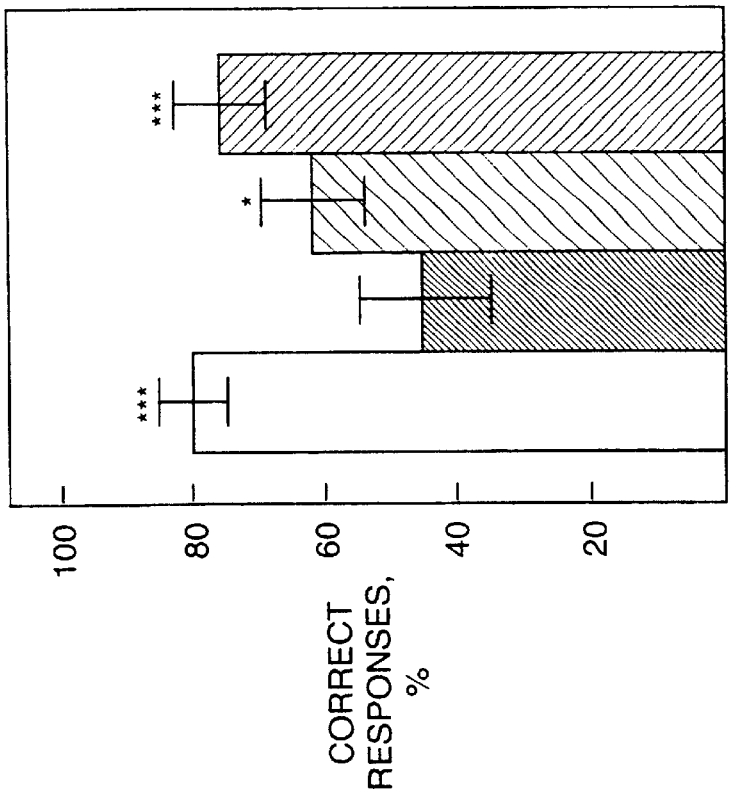

CA-15 (3 mg/kg, p.o., daily) improved the performance of AF64A-treated rats in retention paradigm of the active avoidance test (FIG. 4B). CA-15 demonstrated the strong tendency (although not reaching the level of statistical significance) towards the improvement of the learning ability of the AF64A-treated rats (FIG. 4A).

The effect of CA-18 was studied in two doses: 0.3 and 1 mg/kg (p.o., daily). The lower dose of CA-18 (0.3 mg/kg,) completely restored rats performance in the learning (FIG. 6A) and retention. (FIG. 6B) paradigms of the active avoidance test. The higher dose of CA-18 (1 mg/kg) demonstrated the strong tendency (although not reaching the level of statistical significance) towards the improvement of the learning (FIG. 5A) but not in retention (FIG. 5B) ability of the AF64A-treated rats.

Although we did not plan to perform the special evaluation of the general locomotor activity, we did notice the unspecified sedative effect in rats treated with melatonin (3 mg/kg) starting from the 3–4$^{TH}$ days of treatment and in rats treated with NAS (1 mg/kg) starting from the 6$^{TH}$ day of treatment.

Melatonin (0.3 mg/kg) and CA-18 (0.3 an 1 mg/kg) did not induced sedation in rats.

Morris Water Maze Test.

AF64A significantly increased the response time in comparison to rats treated with the vehicle (CSF) (FIGS. 7A and 7B). Melatonin and CA-18 (0.3 mg/kg, daily) decreased the response time of AF64A-treated rats. Only the results observed on day 1 (FIG. 7A) and day 5 (FIG. 7B) are presented.

Neuronal Cell Culture.

Example 4 showed that exposure of mature cultures of CGC against the fragment of βAP reduced the cell viability in dose-dependent manner ($IC_{50}$=25 μM). Morphological changes (shrinkage of the body and fragmentation of neurites) were observed only when cells were exposed to βAP for 3 days or longer (S. Bachurin et al., *J. Neurochem.* 71 (Suppl). 1:S68). In the present study we used βAP in concentration of 25 μM to evaluate the ability of the compounds to protect neurons against β-amyloid neurotoxicity. Incubation of cultures only with NAS or melatonin in concentration range 25–200 μM increased the amount of living CGC by 16–28% or 3–10% of control, respectively. The viability of neurons exposed to 25 μM βAP was 58±7% (mean ±SEM) of control while co-incubation of cultures with 25 μM NAS and 25 mM βAP resulted in increase of viable neurons up to 101±5% of control (FIGS. 8 and 9) in the same conditions. Melatonin and CA-18 at 25 μM protected neurons - against 25 μM βAP (90% and 93% respectively) as well. Melatonin was less effective in preventing βAP toxicity compared to NAS (FIG. 8).

DISCUSSION

The obtained results indicate that chronic administration of NAS, melatonin, and their newly synthesized derivatives, CA-15 and CA-18, improve cognitive performance of AF64A-treated rats in active avoidance and in water-maze tests. Moreover, these compounds exerted a neuroprotective effect against the β-amyloid (25–35)-induced neurotoxicity in the cerebellar granule cell culture. It is known that neurotoxic action of AF64A related, in part, to oxidative stress, and its indexes are persisting up to 4 months (N. V. Gulyaeva et al., *Brain Res.* 726:174–180, 1996). In this vein, one might suggest that antioxidative properties of melatonin, NAS and, possibly, their derivatives, CA-15 and CA-18, are responsible for their neuroprotective effects. Recent studies indicate that antioxidant ability of melatonin is inferior in comparison to NAS, and, at least in one model, melatonin exerted pro-oxidant effect while NAS exerted strong antioxidant action (R. Barsacchi et al., *Free Radical Biology and Medicine* 24:1187–1192, 1998). Traditionally, NAS was considered only as the precursor of melatonin in the process of melatonin biosynthesis from serotonin. Very few researchers pointed out to the effects of NAS, independent from melatonin, i.e., its memory facilitating (N. Satake et al., *Pharm. Biochem. Behav.* 10:449–436, 1979), hypothermic (D. J. Morton et al., *J. Pineal Res.* 4:1–5, 198.7), analgesic (S. Psarakis et al., *Life Sci.* 42:1109–1116, 1988), antihypertensive (G. F. Oxenkrug, *Vopr. Med. Khim.* 43:522–526, 1998; G. F. Oxenkrug, *Acta. Neurol.*, 1999 (in press); G. F. Oxenkrug et al., *Biol. Psych.* 1999, in press), antidepressant (I. V. Prakhie et al., *Intern. J. Neuropsychopharm.* 1:35–40, 1998), and antioxidative action (F. Lezoualeh et al., *J. Pineal Res.* 24:168–178, 1998). NAS, therefore, might be considered not only as-melatonin precursor but as endogenous indolamine with its own biological properties. Since about 30% of melatonin is demethylated back into NAS (R. M. Leone et al., *Endocrinol.* 114:1825–1832, 1984), the antioxidant effect of supraphysiological concentrations of melatonin (P. B. Duell et al., *Clin. Chem.* 44:1931–1936, 1998) might be ascribed to NAS formed from melatonin. It is noteworthy that the very first indication of the NAS involvement in the cognitive processes came from the observation that scotophobin A, the memory neuropeptide, increased dark avoidance behavior in goldfishes via inhibition of NAS methylation into melatonin (N. Satake et al., *Pharm. Biochem. Behav.* 10:449–436, 1979).

Under the in vivo conditions rapid methylation of NAS into melatonin (G. F. Oxenkrug et al., *Intern. J. Neurosci.* 77:237–241, 1994) might limit the effect of NAS. Therefore, the availability of NAS derivatives which would not undergo the in vivo transformation into melatonin might be of therapeutic advantage. Our preliminary experiments indicated that systemic administration of CA-15 and CA-18 did not change the rat pineal levels of NAS and melatonin (Oxenkrug & Requintina, unpublished data). Although all studied compounds attenuated the AF64A-induced cognitive impairment, there were noticeable differences between the effects NAS, melatonin, and their derivatives (Table 1). NAS was apparently the weakest among the studied compounds in the active avoidance test, while it was the strongest in the attenuating of βAP-induced neurotoxicity. Since NAS is rapidly converted into melatonin in rats (G. F. Oxenkrug et al., *Intern. J. Neurosci.* 77:237–241, 1994), the effect of NAS in our in vivo experiments could not be attributed only to NAS but rather to the mixture of NAS and melatonin.

The occurrence of the sedative effect in rats treated with NAS and melatonin, and somewhat delayed appearance of sedation in NAS, than in melatonin-treated rats, suggest that melatonin but not NAS is responsible for the sedative action. The absence of the sedative effect in rats treated with CA-18 might be of therapeutic advantage of the synthetic NAS/melatonin derivatives.

We have found that CA-15 and CA-18 in addition to their positive effect on cognition exerted antihypertensive and antidepressant-like effects (G. P. Oxenkrug et al., *Biol. Psych.*, 1999, in press). The antidepressant-like activity (decreasing the duration of immobility in the mouse tail suspension test) was more pronounced in CA-18 than CA-15-treated rats. The combination of cognition-enhancing and antidepressant effect in the one and the same compound might be of additional therapeutic advantage.

TABLE 1

| No. | Compounds | Daily Dose, mg/kg | Number of rats | Correct responses, % | |
|---|---|---|---|---|---|
| | | | | Learning test | Retention test |
| 1 | Control (i.c.v. CSF) | Solvent | 33 | 79.3 ± 5.4 * | 76.3 ± 6.3 * |
| 2 | AF64A Alone | Solvent | 31 | 37.4 ± 9.8 | 43.8 ± 8.1 |
| 3 | Melatonin | 3 | 9 | 75.4 ± 7.0 ** | 72.2 ± 5.8 * |
| | Melatonin | 0.3 | 11 | 79.0 ± 6.0 * | 83.2 ± 3.2 * |
| 4 | NAS | 1 | 10 | 65.4 ± 8.8 * | 56.0 ± 9.2 ** |
| 5 | CA-15 | 3 | 9 | 61.4 ± 7.4 | 68.0 ± 8.4 ** |
| 6 | CA-18 | 1 | 10 | 50.0 ± 8.8 | 48.1 ± 9.8 |
| | CA-18 | 0.3 | 11 | 84.0 ± 5.4 * | 82.7 ± 5.0 * |

REFERENCES

The following references are cited throughout the specification and are incorporated herein by reference.

Bachurin, S., Lermontova, N., Shevtzova, E., Serkova, T., & E. Kireeva. 1998. Prevention of β-amyloid-induced neurotoxicity by tacrine and dimebon. *J. Neurochem.*, 71(Suppl.1):S68.

Barsacchi, R., Kusmic, C., Damiani, E., Carloni, P., Greci, L., & L. Donato. 1998. Vitamin E consumption induced by oxidative stress in red blood cells is enhanced by melatonin and reduced by N-acetylserotonin. *Free Radical Biol. & Med.* 24:1187–1192.

Duell, P. B., Wheaton, D. L., Shultz, A., & H. Nguyen. 1998. Inhibition of LDL oxidation by melatonin requires supraphysiologic concentrations. *Clin. Chem.* 44: 1931–1936.

Fisher, A., & I. Hanin. 1986. Potential animal models for senile dementia of Alzheimer's type with emphasis on AF64A-induced cholinotoxicity. *Ann. Rev. Pharmacol. Toxicol.* 26:161–181.

Gallo, V., Kingsbury-Balazs, R. & Jorgensen. 1987. The role of depolarization in the survival and differentiation of cerebellar granule cells in culture. *J. Neurosci.* 7:2203–2213.

Gozes, I., Bardea, A., Reshef, A., Zamostiano, R., Zhukovsky, Rubinraut, S., Fridkin M., & D. Brenneman. 1996. Neuroprotective strategy for Alzheimer disease: Intranasal administration of a fatty neuropeptide. *Proc. Natl. Acad. Sci. USA*. 93 : 427–453.

Gulyaeva, N. V., Lazareva, N. A., & N. L. Libe. 1996. Oxidative stress in the brain following intraventricular administration of ethylcholine aziridinium (AF64A). *Brain Res.* 726:174–180.

Leone, R. M., & R. E. Silman. 1984. Melatonin can be differentially metabolized in the rat to produce N-acetyl-serotonin in addition to 6-hydroxy-melatonin. *Endocrinology*. 114: 1825–1832.

Lermontova N, Lukoyanov N, Serkova T and S. Bachurin (1998) Effect of tacrine on deficits active avoidance performance induced by AF64A in rats. *Molecular and Chemical Neuropathology*, 33:51–61.

Lezouale'h, F., Sparapani, M., and C. Behl. 1998. N-acetyl-serotonin (normelatonin) and melatonin protect neurons against oxidative challenges and suppresses the activity of the transcription factor NF-kB. *J. Pineal Res.* 24:168–178.

Longoni, B., Pryor, W. A., & P. Marchiafava. 1997. Inhibition of lipid peroxidation by N-acetylserotonin and its role in retinal physiology. *Biochem. Biophys. Res. Comm.* 233:778–780.

Morton, D. J. 1987. Both hydroxy- and methoxyindoles modify basal temperature in the rat. *J. Pineal Res.* 4:1–5.

Oxenkrug, G. F. and P. J. Requintina (1994) Stimulation of rat pineal melatonin biosynthesis by N-acetylserotonin, *Intern. J. Neurosci.*, 77:237–241.

Oxenkrug, G. F. 1998. N-acetylserotonin and the hypotensive effect of MAO-A inhibition (mini-review). *Vopr. Med. Khim.* 43:522–526. (Russia).

Oxenkrug, G. F. 1999. Antidepressive and antihypertensive effects of MAO-A inhibition: role of N-acetylserotonin. *Acta. Neurol.* (in press).

Oxenkrug, G. F. & P. J. Requintina. 1999. Hypotensive effect of N-acetylserotonin in spontaneously hypertensive rats. *Biol. Psychiat.* (in press).

Oxenkrug, G. F., Bachurin, S. O., Prakhie, I. V., Requintina, P. J., Afanasiev, A., Beznosko, B., Vankin, G., Lermontova, N., & T. Serkova. 1999. Neurobiological effects of the new indolalkylamine derivatives. *Biol. Psychiat.* (in press).

Papolla, M. A., Sos M., Omar, R. A., Bick, D., Hicksonbick, L. M., Reiter, R. J. Ephthimiopoulos, S., & N. K. Robakis. 1997. Melatonin prevents death of neuroblastoma cells exposed to the Alzheimer amyloid peptide. *J. Neurosci.* 17: 1683–1690.

Prakhie, I. V. &, G. F. Oxenkrug, 1998. The effect of nifedipine, Ca++ antagonist, on activity of MAO inhibitors, N-acetylserotonin and melatonin in the mouse tail suspension test. *Intern. J. Neuropsychopharm.* 1:35–40.

Psarakis, S., Brown, G., & L. J. Grota. 1988. Analgesia induced by N-acetyl-serotonin in the central nervous system. *Life Sci.* 42: 1109–1116.

Reiter, R. J., Pablos, M. I., Agapito, T. T., & J. M. Guerrero. 1996. Melatonin in the context of the free radical theory of aging. *Annals New York Acad. Sci.* 362–378.

Satake, N., & B. E. Morton. 1979. Scotophobin A causes dark avoidance in goldfish by elevating pineal N-acetylserotonin. *Pharmac. Biochem. Behav.* 10: 449–436.

Walsh, T, & K. Opello. 1994. The use of AF64A to model Alzheimer disease. In Toxin-Induced Models of Neurological Disorders. Woodruff M. I., Nonneman A. J. (eds): 259–279. Plenum Press, New York, London.

Witting, W., Kwa, I., Eikelenboom, P., Mirmiram., M., & D. Swaab. 1990. Alterations in the circadian rest-activity rhythm in aging and Alzheimer's disease. *Biol. Psych.* 27: 563–572.

What is claimed is:

1. A method of treating a nerve degeneration disease comprising administering to a mammal suffering from or susceptible to said disease a therapeutically effective amount of a compound of the following Formula I:

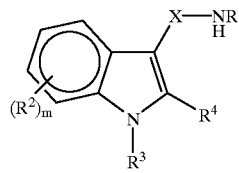

wherein R is —C(=O)R$^1$, —S(O)$_2$R$^1$ or S(O)R$^1$;

R$^1$ is optionally substituted allyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each R$^2$ is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

R$^3$ and R$^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

2. The method of claim 1 wherein X is alkylene having 1 to about 4 carbon atoms.

3. The method of claim 1, wherein X is ethylene.

4. The method of claim 1, wherein R$^3$ and R$^4$ are each hydrogen.

5. The method of claim 1, wherein m is 0, 1 or 2.

6. The method of claim 1, wherein an R$^2$ substituent is present at the 5 or 7 positions of the indole ring.

7. The method of claim 1, wherein an R$^2$ substituent is present at both the 5 and 7 positions of the indole ring.

8. The method of claim 1, wherein a methyl group is at the 7 position of the indole ring.

9. The method of claim 1, wherein R is —C(=O)R$^1$.

10. A method of treating a nerve degeneration disease comprising administering to a mammal suffering from or susceptible to said disease a therapeutically effective amount of a compound of the following Formula II:

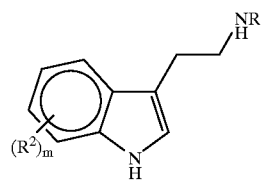

wherein R is —C(=O)R$^1$ or —S(O)$_2$R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each R$^2$ is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable sats thereof.

11. The method of claim 10 wherein m is 0, 1 or 2.

12. The method of claim 10, wherein an R$^2$ substituent is present at the 5 or 7 positions of the indole ring.

13. The method of claim 10, wherein an R$^2$ substituent is present at both the 5 and 7 positions of the indole ring.

14. The method of claim 10, wherein a methyl group is at the 7 position of the indole ring.

15. The method of claim 10, wherein R is —C(=O)R$^1$.

16. A method of treating a nerve degeneration disease comprising administering to a mammal suffering from or susceptible to said disease a therapeutically effective amount of a compound of the following Formula III

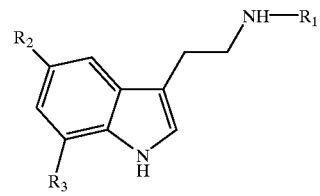

wherein R1 is low Alk—SO$_2$— or; R$^4$—CO— (wherein R$^4$ is low Alk—, low AlkO—, low Alk—NH);

R2 is H, Alk, halogen, R$^5$O— (where R$^5$=H, or PhCH$_2$—); and

R3 is H or Me.

17. The method as in any of claims 1, 10 or 16, wherein the nerve degeneration disease is Alzheimer's disease, Parkinson's disease, Huntington's disease, Amyotrophic Lateral Sclerosis, Down's Syndrome or Korsakoff's disease, Cerebral Palsy, or epilepsy.

18. A method of treating or preventing nerve cell death comprising administering to a mammal suffering from or susceptible to nerve cell death a therapeutically effective amount of a compound of the following Formula I:

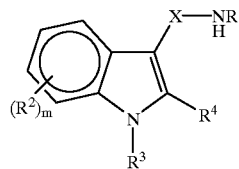

wherein R is —C(=O)R$^1$, —S(O)$_2$R$^1$ or S(O)R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each R$^2$ is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

R$^3$ and R$^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

19. A method of treating or preventing nerve cell death comprising administering to a mammal suffering from or susceptible to nerve cell death a therapeutically effective amount of a compound of the following Formula II:

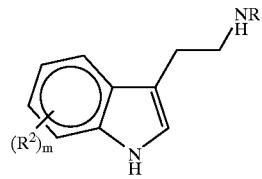

wherein R is —C(=O)R$^1$ or —S(O)$_2$R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each R$^2$ is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable salts thereof.

20. A method of treating or preventing nerve cell death comprising administering to a mammal suffering from or susceptible to nerve cell death a therapeutically effective amount of a compound of the following Formula III

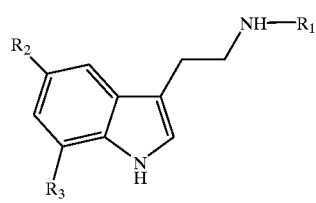

wherein R1 is low Alk—SO$_2$— or; R$^4$—CO— (wherein R$^4$ is low Alk—, low AlkO—, low Alk—NH);

R2 is H, Alk, halogen, R$^5$O— (where R$^5$=H, or PhCH$_2$—); and

R3 is H or Me.

21. The method of any of claims 18, 19, or 20 wherein the nerve cell death is caused by hypoxia, hypoglycemia, brain or spinal cord ischemia, retinal ischemia, brain or spinal cord trauma, heart attack or stroke.

22. A method of treating a mammal suffering from or susceptible to stroke comprising administering to the mammal a therapeutically effective amount of a compound of the following Formula I:

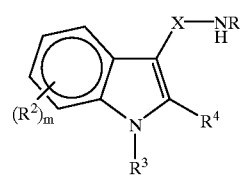

wherein R is —C(=O)R$^1$, —S(O)$_2$R$^1$ or S(O)R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each R$^2$ is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

$R^3$ and $R^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

23. A method of treating a mammal suffering from or susceptible to stroke comprising administering to the mammal a therapeutically effective amount of a compound of the following Formula II:

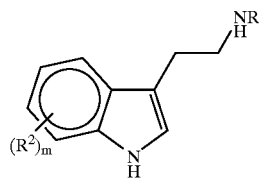

wherein R is —C(=O)$R^1$ or —S(O)$_2R^1$;

$R^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each $R^2$ is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable salts thereof.

24. A method of treating a mammal suffering from or susceptible to stroke comprising administering to the mammal a therapeutically effective amount of a compound of the following Formula III

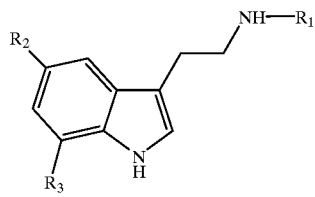

wherein R1 is low Alk—SO$_2$— or; $R^4$—CO— (wherein $R^4$ is low Alk—, low AlkO—, low Alk—NH);

R2 is H, Alk, halogen, $R^5$O— (where $R^5$=H, or PhCH$_2$—); and

R3 is H or Me.

25. A method of treating a mammal suffering from or susceptible to brain or spinal cord trauma or ischemia, or heart attack comprising administering to the mammal a therapeutically effective amount of a compound of the following Formula I:

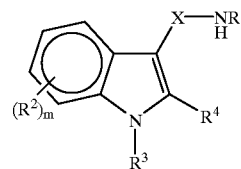

wherein R is —C(=O)$R^1$, —S(O)$_2R^1$ or S(O)$R^1$;

$R^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each $R^2$ is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

$R^3$ and $R^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

26. A method of treating a mammal suffering from or susceptible to brain or spinal cord trauma or ischemia, or heart attack comprising administering to the mammal a therapeutically effective amount of a compound of the following Formula II:

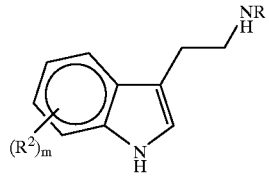

wherein R is —C(=O)$R^1$ or —S(O)$_2R^1$;

$R^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each R² is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or,4; and pharmaceutically acceptable salts thereof.

27. A method of treating a mammal suffering from or susceptible to brain or spinal cord trauma or ischemia, or heart attack comprising administering to the mammal a therapeutically effective amount of a compound of the following Formula III

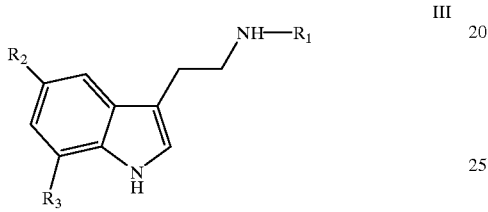

wherein R1 is low Alk—SO₂— or; R⁴—CO— (wherein R⁴ is low Alk—, low AlkO—, low Alk—NH);

R2 is H, Alk, halogen, R⁵O— (where R⁵=H, or PhCH₂—); and

R3 is H or Me.

28. A method of treating a mammal suffering from or susceptible to post-surgical neurological deficits or neurological deficits associated with cardiac arrest, comprising administering to the mammal a therapeutically effective amount of a compound of the following Formula I:

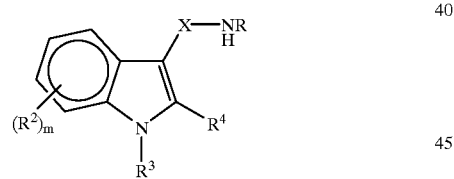

wherein R is —C(=O)R¹, —S(O)₂R¹ or S(O)R¹;

R¹ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each R² is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

R³ and R⁴ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

29. A method of treating a mammal suffering from or susceptible to post-surgical neurological deficits or neurological deficits associated with cardiac arrest, comprising administering to the mammal a therapeutically effective amount of a compound of the following Formula II:

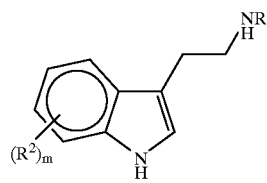

wherein R is —C(=O)R¹ or —S(O)₂R¹;

R¹ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

each R² is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable salts thereof.

30. A method of treating a mammal suffering from or susceptible to post-surgical neurological deficits or neurological deficits associated with cardiac arrest, comprising administering to the mammal a therapeutically effective amount of a compound of the following Formula III

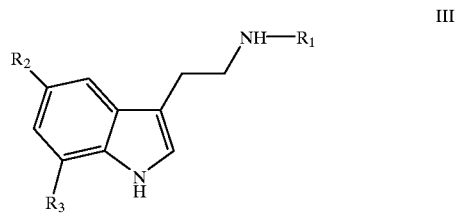

wherein R1 is low Alk—SO₂— or; R⁴—CO— (wherein R⁴ is low Alk—, low AlkO—, low Alk—NH);

R2 is H, Alk, halogen, R⁵O— (where R⁵=H or PhCH₂—); and

R3 is H or Me.

31. A method of preventing age-associated cognitive decline in a human comprising administering to the human an effective amount of a compound of the following Formula I:

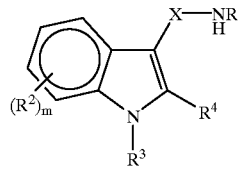

I wherein R is —C(=O)R$^1$, —S(O)$_2$R$^1$ or S(O)R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members in each ring and from 1 to about 3 hetero atoms;

X is a chemical bond, optionally substituted alkylene, optionally substituted alkenylene, optionally substituted alkynylene, optionally substituted heteroalkylene, optionally substituted heteroalkenylene, optionally substituted heteroalkynylene; each R$^2$ is independently optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

R$^3$ and R$^4$ are each independently hydrogen, halogen, optionally substituted alkyl, optionally substituted alkenyl, optionally substituted alkynyl, optionally substituted alkoxy, optionally substituted alkylthio, optionally substituted alkylsulfinyl, optionally substituted alkylsulfonyl, optionally substituted aminoalkyl, optionally substituted carbocyclic aryl, or optionally substituted aralkyl;

m is 0 (i.e. where the fused benzene ring would be fully hydrogen-substituted), 1, 2, 3 or 4; and pharmaceutically acceptable salts thereof.

32. A method of preventing age-associated cognitive decline in a human comprising administering to the human an effective amount of a compound of the following Formula II:

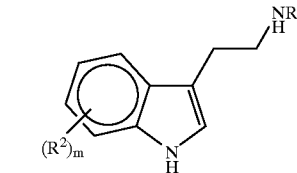

wherein R is —C(=O)R$^1$ or —S(O)$_2$R$^1$;

R$^1$ is optionally substituted alkyl; optionally substituted alkoxy; optionally substituted aminoalkyl; optionally substituted carbocyclic aryl; an optionally substituted alkylaryl; or an optionally substituted heteroaromatic or heteroalicyclic group having from 1 to 3 rings, 3 to about 8 ring members -in each ring and from 1 to about 3 hetero atoms;

each R$^2$ is independently hydrogen, optionally substituted alkyl; optionally substituted alkenyl; optionally substituted alkynyl; optionally substituted alkylthio; optionally substituted alkylsulfinyl; optionally substituted alkylsulfonyl; optionally substituted or unsubstituted carbocyclic aryl; or an optionally substituted heteroaromatic or heteroalicyclic group having from 1 to 3 rings, 3 to about 8 ring members in each ring and 1 to about 3 hetero atoms;

m is 0 (i.e. where the fused benzene ring would be fully hydrogen-substituted), 1, 2, 3 or 4; and pharmaceutically acceptable salts thereof.

33. A method of preventing age-associated cognitive decline in a human comprising administering to the human an effective amount of a compound of the following Formula III.

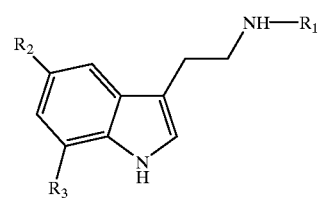

III wherein R1 is low Alk—SO$_2$— or; R$^4$—CO— (wherein R$^4$ is low Alk—, low AlkO—, low Alk—NH);

R2 is H, Alk, halogen, R$^5$O— (where R$^5$=H, or PhCH$_2$—); and

R3 is H or Me.

* * * * *